United States Patent [19]
Hosaka et al.

[11] 3,931,914
[45] Jan. 13, 1976

[54] POWDER EJECTOR

[75] Inventors: Hideo Hosaka, Takasaki; Yasuo Kawamata, Gunma, both of Japan

[73] Assignee: Max Kabushiki Kaisha, Tokyo, Japan

[22] Filed: June 3, 1974

[21] Appl. No.: 475,836

[30] Foreign Application Priority Data

| July 13, 1973 | Japan | 48-83203[U] |
| July 13, 1973 | Japan | 48-83202[U] |
| July 13, 1973 | Japan | 48-83201[U] |
| July 11, 1973 | Japan | 48-82811[U] |
| July 11, 1973 | Japan | 48-83810[U] |
| July 10, 1973 | Japan | 48-81705[U] |
| July 10, 1973 | Japan | 48-81707[U] |
| July 10, 1973 | Japan | 48-81706[U] |
| July 11, 1973 | Japan | 48-82809[U] |
| July 11, 1973 | Japan | 48-82808[U] |

[52] U.S. Cl. .............. 222/193; 222/333; 239/332
[51] Int. Cl.² .................................. B67D 5/54
[58] Field of Search .............. 222/193, 333, 323; 285/302, 331; 136/166, 170, 171; 47/1.41; 239/332, 362, 363, 355

[56] References Cited
UNITED STATES PATENTS

| 1,048,855 | 12/1912 | Murdock | 285/331 |
| 2,421,183 | 5/1947 | Cakebread | 222/193 |
| 3,379,373 | 4/1968 | Roberts | 222/193 X |
| 3,462,082 | 8/1969 | Everett | 222/193 X |
| 3,629,793 | 12/1971 | Ettischer et al. | 136/166 X |
| 3,831,606 | 8/1974 | Damani | 222/193 X |

*Primary Examiner*—Robert B. Reeves
*Assistant Examiner*—Joseph J. Rolla
*Attorney, Agent, or Firm*—Woodhams, Blanchard and Flynn

[57] ABSTRACT

A powder ejector comprising a casing having a pump mounted thereon and driven by a motor. The casing defines a battery confinement space which is accessible through an openable cover. The batteries positioned within the space are connected with the motor by an electrical circuit which is suitably opened and closed by a manually actuatable trigger switch device. A powder container is removably mounted on the casing and an air pipe communicates between the motor and the powder container for pressurizing same. The casing has a nozzle mounted thereon, and a transmission pipe communicates between the powder container and the nozzle for permitting powder to be ejected.

9 Claims, 13 Drawing Figures

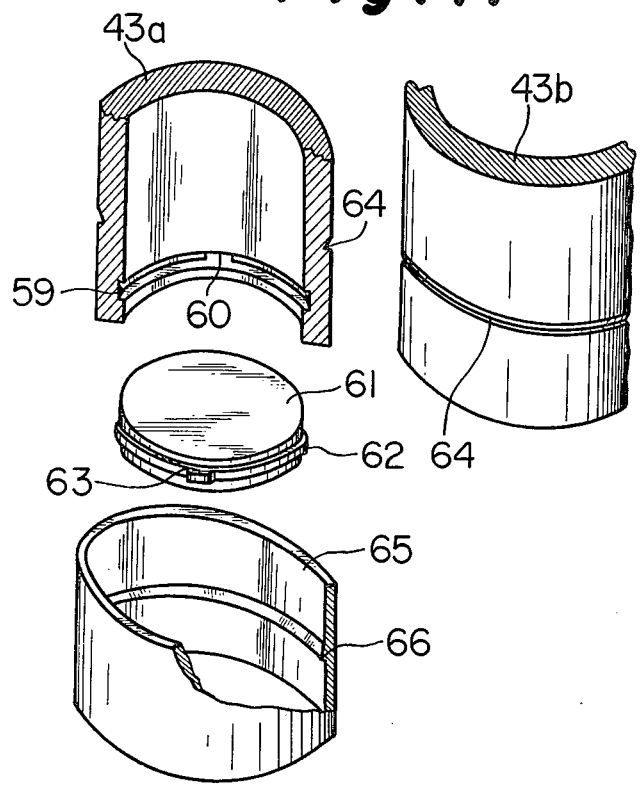

POWDER EJECTOR

FIELD OF THE INVENTION

This invention relates to an improved device for ejecting powder, such a pollen or the like.

BACKGROUND OF THE INVENTION

While numerous devices for ejecting powdery substances have been devised, most of these devices have been extremely complex, both mechanically and structurally, so that use of same has been rather cumbersome. Further, many of these devices have been rather bulky and thus not suitable for hand-held operation. Of the hand-held devices available, most of these devices have not provided for simple and easy operation, so that they have been extremely tiring to the laborer. These known devices have also not permitted use for long periods of time while permitting control over the uniformity of the quantity of powder or product discharged.

Thus, the present invention relates to an improved powder ejector which is convenient and simple to use, as well as simple and easy to assemble and disassemble. The improved powder ejector is also extremely small and lightweight so as to be convenient for manual use, with the device of the present invention being suitable for support and operation by a single hand of a user. The device of the present invention, by having a pistol-shaped configuration, is particularly adaptable for being hand held. The device also incorporates desirable control structure for permitting the quantity of discharged powder to be maintained substantially uniform over long periods of use.

BRIEF DESCRIPTION OF THE DRAWINGS

FIG. 11 is an exploded perspective view, partially cut away, of the powder container.

DETAILED DESCRIPTION

Figure 1:
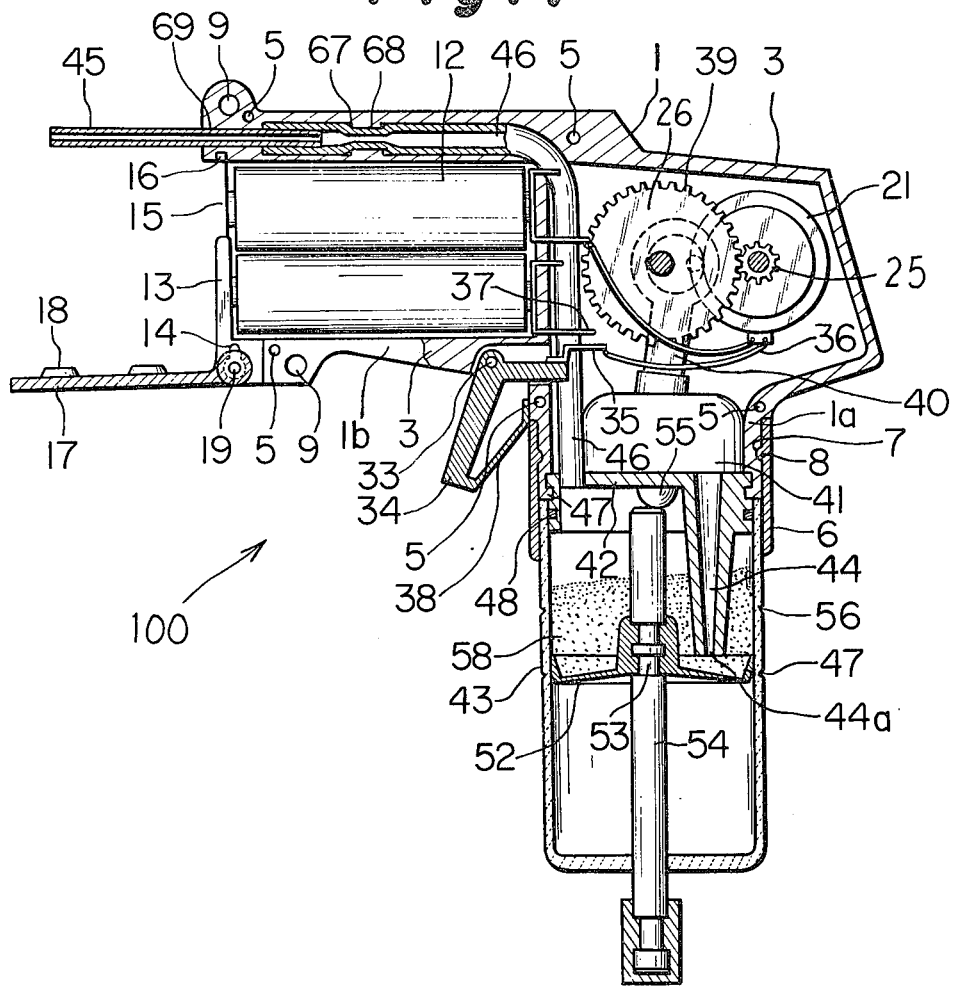
FIG. 1 is a front elevational view, taken in cross section, of the powder ejector.
Figure 2:
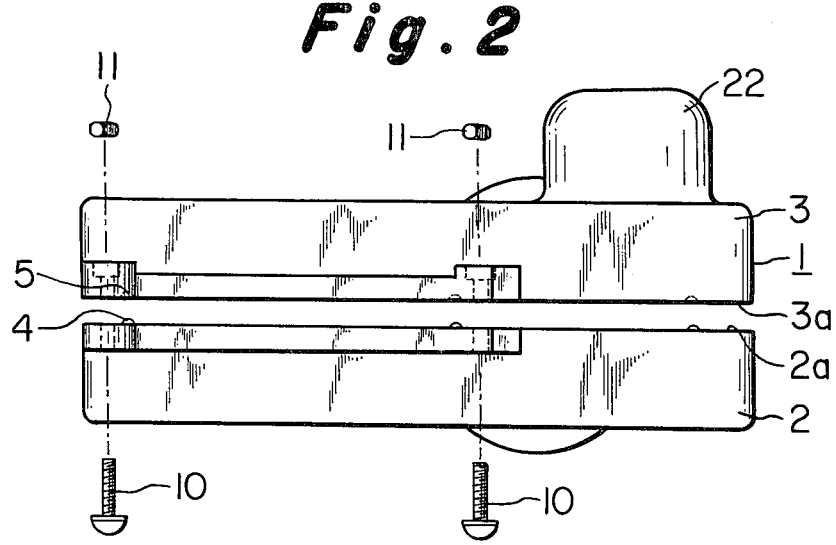
FIG. 2 is an exploded plan view of the powder ejector.

As shown in FIGS. 1 and 2, the powder ejector 100 includes a casing or body 1 made of synthetic resin or the like and divided longitudinally into two casing sections 2 and 3. A plurality of dowels 4 are formed in a protruding or convex manner at proper portions on the joint surface 2a of one casing section 2, and a plurality of dowel holes 5 are formed in a debossed or concave manner correspondingly at proper portions on the joint surface 3a of the other casing section 3 so that the dowels 4 may be properly fitted therein. A casing portion 1a projects downwardly at the rear end of the casing 1 and has a sleeve 6 hermetically fixed on the outer peripheral surface thereof. The projecting section 1a has a recess 7 formed therein, and the sleeve 6 has a projection 8 fitted in said recess 7 to thus ensure tight fitting and engagement thereof with each other.

The casing sections 2 and 3 have a plurality of apertures 9 drilled therein, and a bolt 10 is set through each pair of aligned apertures tightly tied by a nut 11 for fixing the casing sections 2 and 3 in an integrated manner. The upper portion 1b of casing 1 has a space 12 for receiving a plurality of batteries A, and the space 12 has an opening 13 for inserting the batteries A therein. The wall defining the opening 13 has an oblong hole 14 drilled through both sides at the lower end thereof, a notched portion 15 properly formed on both sides at the upper end thereof, and a groove 16 formed on the internal wall surface at the upper end thereof along the upper brim.

Figure 3:
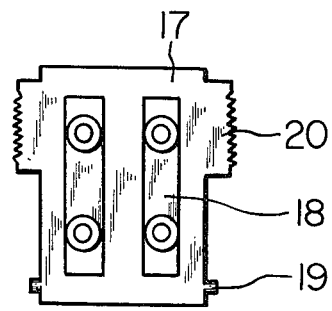
FIG. 3 is a plan view of a cover for the battery housing.

A cover 17 (see FIGS. 1 and 3) has a plurality of electroconductive metal contact pieces 18 positioned so as to come into contact with the terminals of the batteries A. The cover 17 has a pin 19 properly set in place in a protruding manner on both sides thereof at the lower end, which pin 19 is so fitted in the oblong hole 14 as to be free to slide and turn. Cover 17 also has lug pieces 20 projecting from both sides and positioned so as to engage the notched portions 15, and the cover 17 further has the upper brim thereof subjected to pressure fit within the groove 16.

Figure 4:
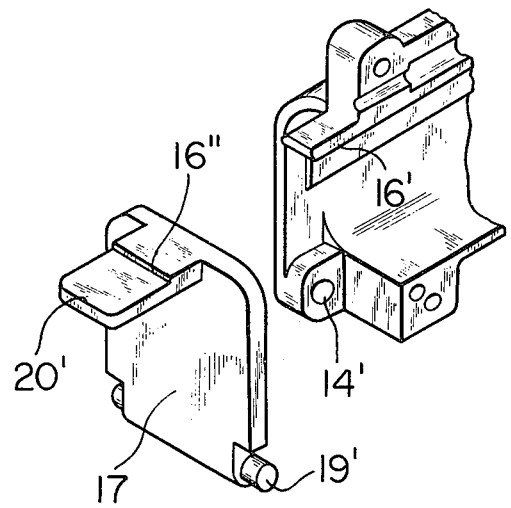
FIG. 4 is a perspective view in a disassembled state, of another embodiment of the cover for the battery housing.

In another embodiment of the cover 17', as shown in FIG. 4, a hole 14' is formed on the internal surface of the casing on both sides of the opening 13, and the upper end of casing 1 is extended to form a projection or step 16'. The cover 17' has a pin 19' properly formed in such a manner as to be rotatably fitted in the hole 14', and the cover is provided with an elastic finger grip 20' having a step 16" adapted to be engaged with the step 16'. The cover 17' has such a shape as to be fitted in the opening 13. Thus, the cover 17' is opened and closed by means of the finger grip 20'.

Figure 5:
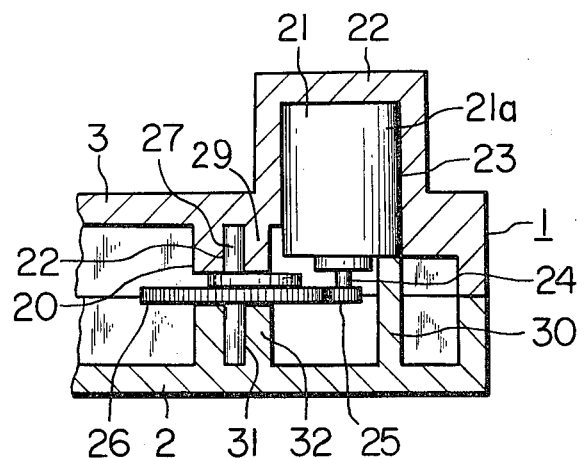
FIG. 5 is a fragmentary sectional view of the driving gear mechanism for the pump.
Figure 6:
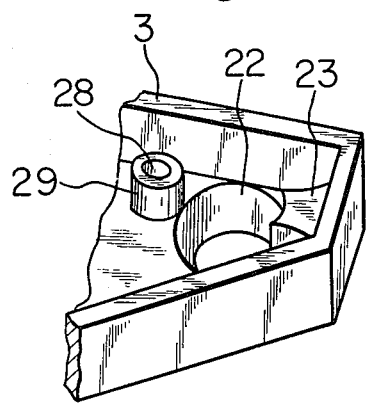
FIG. 6 is a fragmentary perspective view of a portion of the upper casing section shown in FIG. 5.
Figure 7:
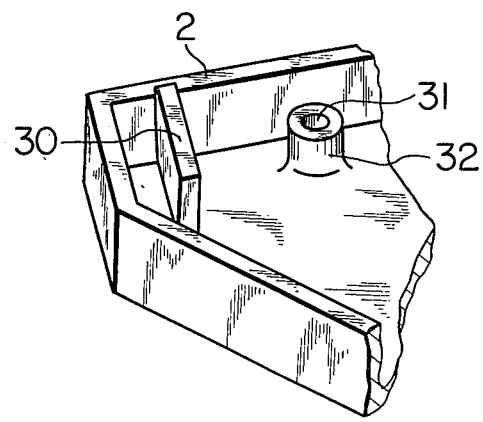
FIG. 7 is a fragmentary perspective view of a portion of the lower casing section shown in FIG. 5.

The casing 1 has a projecting portion 22 formed on the rearward end thereof, which portion 22 is capable of having a motor 21 fitted therein. As shown in FIGS. 5–7, the check piece 23 on the casing contacts a flat surface 21a formed on the peripheral surface of the motor 21 and prevents the housing of the motor 21 from revolving. A bearing section 29 is formed on the casing section 3 and has a bearing hole 28 which rotatably supports a follower shaft 27. The shaft 27 has a follower gear 26 fixed thereon and engaged with a gear 25 fixed to the revolving shaft 24 of the motor 21.

The other casing section 2 has a protruding bearing section 32 and a protruding stop piece 30 for preventing the motor 21 from moving in the axial direction. The bearing section 32, which contains therein a bearing hole 31, rotatably supports the follower shaft 27.

A trigger 34 made of hard resin material is pivoted on the body 1 by means of a pin 33. An S-shaped terminal board 35 of metal plate is fixed on the upper end of trigger 34 and is connected with one end of a conductor 36, which conductor has the other end thereof connected to the motor 21. The terminal board 35 confronts a stationary terminal plate 37 which is in contact with the terminals of the batteries A, so that plate 35 is capable of moving into and out of contact with plate 37.

The trigger 34 is provided, at the lower section thereof, with an elastic spring piece 38 which engages the casing and resiliently urges the trigger 34 outwardly such that the terminal board 35 is caused to be separated from the terminal board 37. Spring piece 38 also causes the lower surface of the upper leg of the trigger 34 to contact the body 1 to thus define the open position of the plate 35.

The motor 21, when energized by the trigger 34, drives gear 26 having a crank 39 which reciprocates a connecting rod 40. The rod 40 in turn operates a pump 41.

The pump 41 is set in place on a base plate 42 secured at the lower end of the casing section 1a, and the base plate 42 has an air pipe 44 which supplies compressed air from the pump 41 into the interior of a powder container 43 through a one-way check valve (not shown). A flexible pipe 46 for discharging the powder 58 is connected at one end thereof to the plate 42, and is connected with a nozzle pipe 45 that protrudes over the top end of the casing 1. A ring-shaped concave groove 47 formed on the outer peripheral surface of the base plate 42 has an elastomeric O-ring 48 properly fitted therein, to thus be fitted on the internal wall of the powder container 43. Furthermore, a sleeve 6 is pressure fitted on the outer periphery of casing section 1a, whereby the powder container can be hermetically fitted into the void formed by the base plate 42 and the sleeve 6 in such a manner as to be capable of being removed or replaced as desired.

Figure 9A:
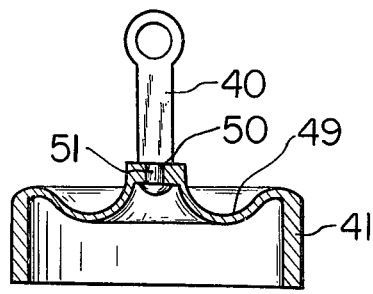
FIG. 9A is an explanatory drawing for setting a pump and a connection rod in place.
Figure 9B:
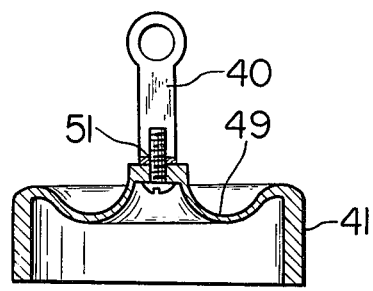
FIGS. 9B and 9C show conventional means for connecting a pump to a rod.
Figure 9C:
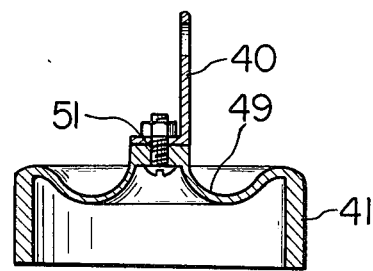

The pump 41 (see FIG. 9A) has a tiny hole 50 drilled at the center of a flexible end wall 49, and the connecting rod 40 has a pin 51 on the lower end thereof engaged within the hole 50 to connect the rod 40 to the flexible film 49 while maintaining the pump sealed. As shown in FIGS. 9B and 9C, the connecting rod 40 can be secured to film 49 by means of a screw set.

The powder container 43, as shown in FIG. 1, has a piston 52 for controlling the feed of the powder, which piston 52 is made of synthetic resin or the like and is fitted within container 43 in such a manner as to be free to slide. An adjusting rod 54 with ring-shaped concave groove 53 properly formed at the center thereof is formed in an integrated manner so as to protrude above and below the piston 52, the adjusting rod 54 thus protruding downward so as to slidably extend through the bottom plate of the powder container 43. The top end of the rod 54 comes into contact with a projection 55 formed on the lower surface of the base plate 42, whereby the upward thrust of the piston 52 is limited. The lower end opening 44a of the air pipe 44 is thus prevented from being stopped or covered by the piston 52.

The powder container 43, on a part thereof, is made of either a transparent substance or a semitransparent substance, and either the outer peripheral surface or the inner peripheral surface thereof has an uppermost limit calibration mark 56 (FIG. 1) at a position slightly higher than the lower end opening 44a of the air pipe 44, and has a lowermost limit calibration mark 57 at a position slightly lower than the lower end opening 44a of the air pipe 44, for ensuring proper indication.

The powder container 43, as shown in FIG. 11, may comprise a pair of longitudinally halved casing pieces 43a and 43b. The pieces 43a and 43b have a ring-shaped concave groove 59 formed on the internal peripheral surface thereof at a position near the lower end thereof, and have a concave hole 60 properly formed at a portion of the groove 59. A disk-shaped bottom plate 61, on the part thereof, has a ring-shaped convex thread or rib 62 formed on the peripheral surface thereof, and also has a lug 63 formed on a portion of the ring-shaped thread 62. The casing pieces 43a and 43b have another ring-shaped concave groove 64 formed on the outer peripheral surface thereof, and there is also provided a sleeve 65 having a ring-shaped projection 66 properly formed on the inner peripheral surface thereof. The convex thread 62 and the lugs 63 formed on the bottom plate 61 are properly fitted in the concave groove 59 and the concave holes 60 of the casing pieces 43a and 43b, respectively, to thus fabricate the casing pieces 43a and 43b into a cylindrical shape. The cylinder is then pressure fitted into the sleeve 65, to thus fit the ring-shaped projection 66 into the concave groove 64, whereby all component parts are integrated into a unified entity.

The flexible pipe 46 for discharging the powder is set in place through a hole 67 drilled in the casing 1, and the pipe 46 is nipped in place by a holder 68 formed in a protruding manner in the hole 67. One end of the flexible pipe 46 is positioned so as to open into the interior of the powder container 43, while the other end of the pipe 46 is disposed in communication with insertion hole 69 for the nozzle pipe 45.

OPERATION

Figure 8:
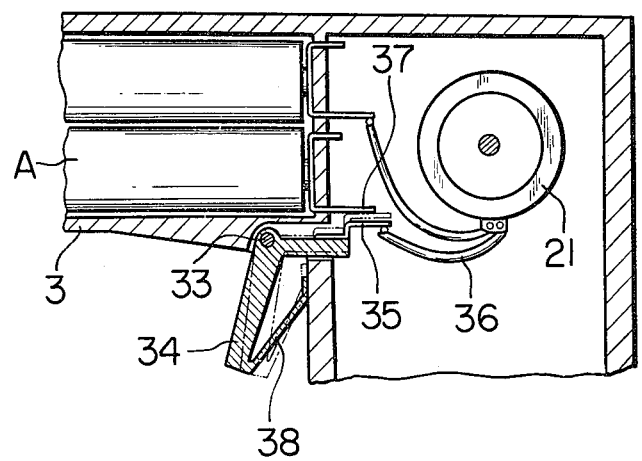
FIG. 8 is an explanatory drawing of the action of a switch associated with the trigger.
Figure 10:
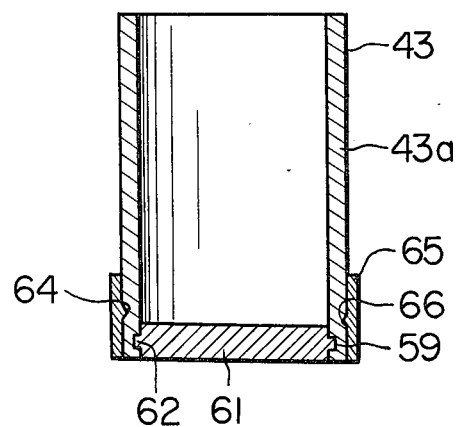
FIG. 10 is a section of a powder container.

When the trigger 34 is pressed rightwardly against the urging of the elastic spring piece 38, the terminal plates 35 and 37 come in contact with each other (see FIG. 8) to effect electrification of motor 21. The motor 21 rotates the gear wheel 26 and the crank 39, whereby the connecting rod 40 reciprocates the flexible end wall 49 of the pump 41. This causes air to be supplied from the pump compartment through the pipe 44 into the powder chamber so as to pressurize same. This in turn causes the air and the powder 58 to flow through the pipe 46 whereby it is discharged by nozzle 45.

When the quantity of powder 58 in the powder container 43 is reduced, the piston 52 is pushed upward by a proper operation of the adjusting rod 54, and the volume ratio of the powder to the air in the container is properly controlled so as to be fairly constant, thus keeping the quantity of the powder discharged from the nozzle 45 fairly uniform. When the top end of the adjusting rod 54 comes in contact with the stop 55, the piston 52 is prevented from being pushed up further and the lower end opening 44a of the air pipe is kept free.

Since the powder container 43 is either transparent or semitransparent, a reduction in the quantity of the powder 58 in the container can be visually observed. Whenever the top level of the powder reaches the lowermost calibration mark 47, the powder-to-air ratio can be maintained at a fairly constant level by pushing the piston 52 upwardly until the top level of the powder moves upwardly to a position adjacent the uppermost calibration mark 56.

Since the powder container 43 is pressure fitted and fixed in place through the O-ring 48 arranged in the interposed interstice formed by the sleeve 6 and the base plate 42, the powder container 43 can be set in, and off, very readily. Further, the airtight state produced by the O-ring 48 at the time of mounting the powder container 43 in place keeps the powder container pressurized. Further, since the powder container 43 is set in place in a secure manner by the employment of the sleeve, a spare container which has been prepared in advance for use with supplementary powder can be properly set in place to replace an emptied container, thus enabling the ejection operation to be continued as long as desired.

An elastically flexible metal piece 18 set in place on the cover 17 resiliently presses the battery assembly A into the space 12 when the cover 17 is closed, thus enabling secure housing of the batteries free from floating, and concurrently enabling the battery assembly A to be instantly electrified by making connection of the terminals of a plurality of batteries (four batteries in the illustrated embodiment) and pulling the trigger 34, until the motor 21 is energized. The battery assembly A can be anchored in a secure manner by moving the pin 19 upwardly after the cover 17 has been closed, thereby fitting the top end of the cover into the groove 16. By virtue of the outward thrusting force created by the elasticity of the elastic contact metal piece 18, the cover 17 is held closed.

The flexible pipe 46 for discharging powder is held in place by a holder 68 set in place in a protruding manner in the hole 67. The nozzle of the pipe 45 is fixed to the flexible pipe 46 in such a manner as to be mounted on, or removed, as desired. Since the casing 1 and the powder container 43 are assembled into an integrated entity in such a manner as to be separable, they can be disassembled at the time of packaging and transportation, while at the time of the use thereof, the components can be readily assembled, followed by integration thereof into a unified entity by the employment of bolts 10, nuts 11, and the sleeve 6, and hence a solid powder ejector device is obtainable. The sleeve 6 serves for the elimination of an incongruous sense of a convex and a concave along the crevices of the powder ejector as felt on the holding section, to thus excite a comfortable feeling during operation.

What is claimed is:

1. In a portable hand-held powder dispensing device, comprising in combination:
    portable housing means defining therein a substantially closed equipment chamber and a battery containment space, said housing means having an opening formed therein for communication with said space;
    a powder storage container fixedly attached to said housing means and defining therein a compartment adapted to contain a quantity of powder;
    pump means mounted on said housing means and positioned within said chamber for supplying air into said compartment, said pump means having a discharge port connected so as to communicate with said compartment;
    electrical motor means for driving said pump means, said motor means being mounted on said housing means and disposed within said chamber;
    battery means disposed within said space for energizing said motor means;
    cover means swingably mounted on said housing means for closing said opening, said cover means being hingedly connected along one edge thereof to said housing means, the opposite edge of said cover means cooperating with said housing means to create a pressure fit therebetween when in a closed position, the cover means also having electroconductive metal contact means positioned on the inner surface thereof for contact with terminals on the battery means when the cover means is closed;
    conduit means providing communication between said compartment and a location disposed externally thereof for permitting discharge of powder from said compartment, said conduit means having the inlet end thereof positioned in communication with said compartment and having a discharge member on the outlet end thereof;
    electrical switch means mounted on said housing means for electrically connecting said battery means and said motor means together to permit energization of said motor means when said switch means is closed; and
    manually actuated means movably supported on said housing means and coacting with said switch means for permitting selected actuation of said switch means.

2. A device according to claim 1, wherein said housing means includes elongated grooves formed therein and disposed on opposite sides of said opening adjacent one edge thereof, said cover means having on both sides thereof a pin which projects outwardly from the cover means and is fitted within the elongated groove in a manner so as to be free to both rotate within said groove and slide therealong, said housing means also having a further elongated groove formed therein and extending along one side of said opening and said cover means having said opposite edge thereof extending into said further elongated groove for creating a pressure fit between the cover means and the housing means.

3. A device according to claim 1, wherein the housing means has a pair of holes formed therein on opposite sides of said opening adjacent said one edge of said cover means, said cover means having a pair of pins fixed thereto and projecting outwardly from opposite sides of said cover means so as to extend into said holes, said cover means also having a stepped projection fixed thereto adjacent the opposite edge thereof and projecting outwardly from the outer surface of said cover means, said stepped projection having a portion thereof adapted to be engaged with a flange on said housing means to create a pressure fit therebetween when the cover means is closed, said stepped projection also including a further portion spaced outwardly from the first-mentioned portion to provide a finger grip.

4. A device according to claim 1, wherein said housing means is formed by a pair of housing halves which have abutting contact surfaces so that said housing halves when fixedly connected coact to define said space and said chamber therebetween, the contact surface of one of the housing halves having a plurality of dowels projecting therefrom, and the contact surface of the other housing half having a plurality of dowel holes therein for receiving said dowels to permit the housing halves to be fixedly connected together, each of said housing halves having a half shell section which coacts with the half shell section on the other housing half when they are fixedly connected together to form a sleevelike shell, and a sleeve member engaged with and disposed in surrounding relationship to the sleevelike shell, said sleeve member projecting outwardly beyond the end of said sleevelike shell, and said powder storage container having an edge portion thereof which is slidably inserted into and engaged by said sleeve member.

5. A device according to claim 1, including adjustment means associated with the powder storage container for varying the volume of said compartment, said adjustment means including a piston slidably fitted within the container and a regulating element connected to the piston and projecting outwardly of the container to permit the position of the piston within the container to be selectively varied, said piston also having a control element projecting therefrom and adapted to coact with the housing means for limiting the displacement of the piston and hence the minimum volume of the compartment.

6. A device according to claim 5, including a discharge pipe connected to the discharge port of said pump means and extending into the interior of said compartment so that the outlet end of said discharge pipe is substantially immersed within the quantity of powder contained within said compartment, said piston being slidably supported within said powder storage container so as to be movable toward said discharge pipe, said regulating element being coaxially aligned and fixedly connected to the piston and projecting away from said piston on the side thereof opposite from said outlet pipe, and said control element being fixed to and coaxially aligned with said piston and projecting axially thereof in a direction opposite from said regulating element.

7. In a portable hand-held powder dispensing device, comprising in combination:
   portable housing means defining therein a substantially closed chamber;
   a powder storage container fixedly attached to said housing means and defining therein a compartment adapted to contain a quantity of powder;
   pump means mounted on said housing means and positioned within said chamber for supplying air into said compartment, said pump means having an air pipe connected to the discharge port of said pump means and extending into said compartment;
   electrical motor means for driving said pump means, said motor means being mounted on said housing means and disposed within said chamber;
   battery means disposed within said chamber for energizing said motor means;
   electrical switch means mounted on said housing means for electrically connecting said battery means and said motor means together to permit energization of said motor means when said switch means is closed;
   manually actuated trigger means movably supported on said housing means and coacting with said switch means for permitting selected actuation of said switch means;
   conduit means providing communication between said compartment and a location disposed externally thereof for permitting discharge of powder from said compartment, said conduit means comprising an elongated flexible conduit having one end portion thereof positioned in communication with said compartment, said housing means having a first elongated bore formed therein and the other end portion of said conduit being snugly accommodated within said first bore, said housing means having a holding section which protrudes sidewardly into said first bore and deforms said conduit for holding said conduit in position, said housing means having a second bore formed therein aligned with said first bore and of smaller diameter, and an elongated discharge pipe having one end portion thereof slidably received within said second bore and slidably inserted into the adjacent end of said conduit, the other end of said discharge pipe projecting outwardly from said housing means and having a discharge opening at the free end thereof.

8. In a portable hand-held powder dispensing device, comprising in combination:
   portable housing mean defining therein a substantially closed chamber, said housing means having a ring-shaped cylindrical end portion defining therein an opening which communicates with said chamber;
   and annular base plate fixed to said end section and extending across said opening for substantially closing same, said base plate having an air supply opening and a powder feed-out opening extending therethrough;
   said end portion and said base plate defining therebetween a ring-shaped groove which projects outwardly to the free end of said end portion, and an elastic O-ring seal member associated with said groove;
   a cup-shaped powder storage container fixedly but removably attached to said housing means and defining therein a compartment adapted to contain a quantity of powder, said container having a free cylindrical edge portion slidably inserted into said ring-shaped groove so as to be interposed between the base plate and the end portion of said housing means, said O-ring seal member being sealingly engaged with said container;
   pump means mounted on said housing means and positioned within said chamber for supplying air into said compartment, said pump means having the discharge port thereof connected to the air supply opening in said base plate so as to communicate with said compartment;
   electrical motor means for driving said pump means, said motor means being mounted on said housing means and disposed within said chamber;
   battery means disposed within said chamber for energizing said motor means;
   manually actuated switch means mounted on said housing means for electrically connecting said battery means and said motor means together to permit energization of said motor means when said switch means is closed; and
   conduit means providing communication between said compartment and a location disposed externally of said housing means for permitting discharge of powder from said compartment, said conduit means having the inlet end thereof connected to said base plate and communicating with said powder feed-out opening, the outlet end of said conduit means having a discharge nozzle associated therewith.

9. A device according to claim 8, wherein said housing means includes two separate housing sections which are fixedly connected together and define said chamber therebetween, said housing sections each having a substantially semicylindrical shell portion thereon, whereby the shell portions on said two housing sections coact to define a part of said end portion when said housing sections are fixedly connected together, said end portion of the housing means further including a one-piece sleeve tightly fitted on and surrounding the cylindrical shell, said sleeve and said base plate projecting axially outwardly beyond the free end of said shell so as to define said ring-shaped groove therebetween.

* * * * *